United States Patent
Haese et al.

(10) Patent No.: US 6,989,468 B2
(45) Date of Patent: Jan. 24, 2006

(54) METHOD FOR THE ISOMERIZATION OF ALLYL ALCOHOLS

(75) Inventors: Frank Haese, Lambsheim (DE); Klaus Ebel, Lampertheim (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 386 days.

(21) Appl. No.: 10/380,116

(22) PCT Filed: Sep. 18, 2001

(86) PCT No.: PCT/EP01/10777

§ 371 (c)(1),
(2), (4) Date: Mar. 11, 2003

(87) PCT Pub. No.: WO02/24617

PCT Pub. Date: Mar. 28, 2002

(65) Prior Publication Data

US 2004/0097765 A1 May 20, 2004

(30) Foreign Application Priority Data

Sep. 20, 2000 (DE) ........................ 100 46 865

(51) Int. Cl.
C07C 29/56 (2006.01)
B01J 31/02 (2006.01)
B01J 31/16 (2006.01)
B01J 35/02 (2006.01)

(52) U.S. Cl. .................. 568/906; 568/902; 502/160; 502/150; 502/305

(58) Field of Classification Search ............. 568/906, 568/902; 502/160, 150, 305
See application file for complete search history.

(56) References Cited

U.S. PATENT DOCUMENTS 5,998,680 A  12/1999  Kiefer et al.

FOREIGN PATENT DOCUMENTS

DE   21 16698   10/1975
EP   860 415    8/1998

OTHER PUBLICATIONS

Patent Abstracts of Japan 52131506.
JO 1196–547–A Derwent Publications.

Primary Examiner—Elvis O. Price
(74) Attorney, Agent, or Firm—Novak Druce & Quigg

(57) ABSTRACT

The present invention relates to a process for the isomerization of precursor allyl alcohols of the formula (I) to product allyl alcohols of the formula (II)

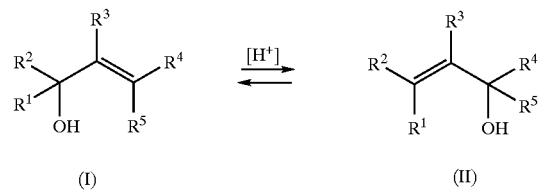

where $R^1$ to $R^5$ are hydrogen or a mono- or polyunsaturated or saturated $C_1$–$C_{12}$-alkyl radical, which may be substituted, in both directions of the equilibrium, wherein the reaction takes place in the presence of an oxoperoxotungsten(VI) complex of the formula (III),

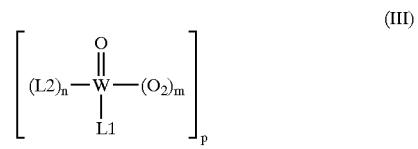

where L1, L2 in each case independently of one another are water or a free coordination site, or are optionally a ligand chosen from the group of aminoalcohols, aminophenols, aminocarboxylic acids or mixtures thereof or mixtures of amines with alcohols, phenols or carboxylic acids, m is the number 1 or 2 n is a number from 1 to 6 p is a number from 1 to 6, where in the case of p>1 a di- or polynuclear complex is formed, and also to novel oxoperoxotungsten(VI) complexes and to the use thereof.

14 Claims, No Drawings

METHOD FOR THE ISOMERIZATION OF ALLYL ALCOHOLS

The present invention relates to a process for the isomerization of precursor allyl alcohols to product allyl alcohols in both directions of the equilibrium, wherein the reaction takes place in the presence of an oxoperoxotungsten(VI) complex, and to novel peroxotungsten(VI) complexes, and to the use thereof.

Allyl alcohols are important intermediates in industrial organic product synthesis. Tertiary allyl alcohols in particular serve, for example, as intermediate compounds in the preparation of fragrances, and also as additives in soaps and detergents.

Allyl alcohols isomerize under acid catalysis. This isomerization corresponds to a 1,3-migration of the hydroxyl group and an internal displacement of the double bond, as shown in the equation below with the formulae I and II:

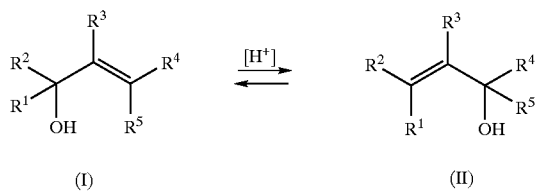

in which the radicals $R^1$ to $R^5$ are hydrogen or a mono- or polyunsaturated or saturated $C_1$–$C_{12}$-alkyl radical, which may be substituted.

The process is particularly suitable for the preparation of tertiary product allyl alcohols, such as, for example, 2-linalool, by isomerization of primary or secondary allyl alcohols, such as, for example, geraniol or nerol.

Geraniol (2-trans-3,7-dimethyl-2,6-octadien-8-ol), nerol (2-cis-3,7-dimethyl-2,6-octadien-8-ol) and 2-linalool (3,7-dimethyl-1,6-octadien-3-ol) are important compounds in the fragrance industry. They are either used directly as fragrances or converted to higher molecular weight fragrances by reaction with other compounds. These terpene alcohols are also of importance as C10 building blocks in the synthesis of vitamins, such as vitamin E and Vitamin A.

In the past the literature has given preference to the description of processes for the isomerization of linalool to geraniol. Since the isomerizations are equilibrium reactions, the processes developed can in principle also be used for the reversed reaction of the isomerization from geraniol or nerol to linalool.

Initially, the isomerization reactions of allyl alcohols were carried out using acids as catalysts. However, these processes were only of limited importance since secondary reactions, such as, for example, dehydrations or cyclizations, dominated them.

Later, molybdenum, vanadium and tungsten compounds were identified and investigated as catalysts for the rearrangement of substituted allyl alcohols (cf. P. Chabardes et al. in *Tetrahedron* 33 (1977), pages 1775–1783.).

Whereas the molybdenum compound described in GB 125 6184 as isomerization catalyst released unsatisfactory reaction results, with tungsten oxo(VI) alkoxide catalysts of the formula $WO(OR)_4$ in the presence of a nitrogen base as additional ligand, relatively high selectivities coupled with simultaneously higher activities, compared with the analogous vanadium oxo(V) alkoxide catalysts of the formula $VO(OR)_3$, were possible. Further advantages of the tungsten catalysts are that, firstly, they can be readily separated off from the reaction mixture (cf. T. Hosogai et al. in *Chemistry Letters* 1982, pages 357–360) and that they have only low toxicity compared with the vanadium catalyst.

Furthermore, DE 25 16 698 discloses the preparation of novel catalysts based on tungsten, and to the use thereof for the catalytic rearrangement of tertiary to primary allyl alcohols. In this process, the catalysts used are tungsten oxo(VI) complexes comprising alkoxy radicals and/or trialkylsilyl radicals bonded via oxygen and which, to improve the selectivity, additionally comprise, bonded coordinately to the tungsten, ligands which contain an element chosen from the elements N, P, As and Bi, in particular ligands chosen from the class of primary, secondary and tertiary monoamines, polyamines, Schiff's bases, imines, nitriles and isonitriles. Ligands which are cited therein as particularly suitable are primary monoamines, such as methylamine, ethylamine, propylamine, b-ethoxyethylamine [sic], butylamine, cyclohexylamine, aniline and naphthylamine; secondary monoamines, such as dimethylamine, diethylamine, dibutylamine, dicyclohexylamine, methylaniline, methylcyclohexylamine, piperidine, morpholine and pyrrolidine; tertiary monoamines, such as trimethylamine, triethylamine, ethyldibutylamine, tricyclohexylamine, dimethylaniline, pyridine, picoline, quinoline, isoquinoline, N-methylpyrrolidine and N-methylmorphoine [sic]; ethylenediamine, pyrazine, piperazine, pyrimidine, triethylenediamine, 1,8-diazabicyclo[5,4,0]undec-7-ene, polyethylenimines, and ion exchanger resins having a large number of amino groups within the molecules, in particular pyridine, triethylamine, cyclohexylamine, diethylamine and tricyclohexylphosphine. Aminoalcohols are not mentioned therein.

Our own investigations into the isomerization of geraniol using a 0.05 mol % strength solution of tungsten oxo(VI) tetrakisgeranylate analogously to the process described in DE 25 16 698 have shown that the rearrangement to linalool proceeds in a significantly more selective manner in the presence of a nitrogen base at 200° C. (reaction time about 1 hour) than without co-use of a nitrogen base. The nitrogen bases used here were diethylamine, pyridine, imidazole and poly-(4-vinylpyridine). Improvements have been achieved by the addition of aminoalcohols to the catalyst solution (see Comparative Experiments, Examples 2 to 6). The selectivities of linalool achieved with this process are very good, although the conversions achieved in the process are still unsatisfactory.

Disadvantages of these experiments were the comparatively lower conversions coupled with simultaneously high temperatures of more than 150° C., which accelerated the formation of byproducts.

DE 25 16 698 describes the synthesis of tungsten alkoxides, by alcoholysis of tungsten oxotetrachloride with alcohols or alkoxides dissolved in alcohols. Although removal of the chloride in the form of ammonium chloride using ammonia or as sodium chloride using sodium methoxide is possible, it is always incomplete. Chlorine is also almost always present in the distilled product allyl alcohol, which severely impairs its quality and acceptance for fragrances and vitamins. In addition, the chloride in the tungsten alkoxide, even in ppm amounts, has a detrimental corrosive action in metal columns and reactors. Subsequent removal of traces of chloride via activated carbon filters or silver(I) oxide is possible, but laborious and makes the overall process complex and more expensive.

In addition, tungsten oxotetrachloride has to first be provided by known methods using tungstic acid and thionyl chloride in an upstream reaction, meaning that the synthesis of tungsten alkoxides has to be carried out with high expenditure in a multistage process.

The process, likewise described in DE 25 16 698, for tungsten oxo(VI) alkoxide complexes starting from tungsten trioxide with hydroxyl compounds cannot be used for industrial applications because of the poor yields.

As is known, tungsten alkoxides are sensitive to hydrolysis and react with water to give alcohol and tungsten oxide. Since dehydration also always takes place as a secondary reaction of the allyl alcohol isomerization, under the conditions of the allyl alcohol isomerization, tungsten oxides increasingly precipitate out from the reaction mixture in sparingly soluble form. These increase the catalyst costs and further favor the formation of byproducts and water from allyl alcohols and lead to further impairment of the selectivity.

It is an object of the invention to improve the process for the isomerization of allyl alcohols such that the tungsten oxo catalyst is halogen-free and can be prepared in simple, cost-effective steps in order to avoid contamination of the allyl alcohol by halogen and, moreover, corrosion problems in the plant. Furthermore, the aim was to reduce or avoid completely catalyst losses caused by hydrolysis, and to improve the product selectivity. There is also the need to accelerate the rate of establishment of an equilibrium, and to increase the space-time yields, without having to further increase the isomerization temperature.

Furthermore, the improved catalysts were, in the case of the isomerization of primary or secondary allyl alcohols, such as geraniol and nerol, to tertiary allyl alcohols, such as linalool, intended to achieve higher conversions of the precursor allyl alcohol used, i.e. to accelerate the rate of establishment of an equilibrium. Furthermore, the novel catalysts were to be easier to prepare than those hitherto.

Surprisingly, we have found that the object is achieved with novel homogeneously dissolved oxoperoxotungsten (VI) complexes of the formula (III), coupled with simultaneously improved selectivity and higher activity for the isomerization of geraniol and nerol to linalool.

According to the invention, it is possible to use either homogeneous solutions of oxoperoxotungsten(VI) in water, alcohol or another solvent.

The invention provides a process for the isomerization of precursor allyl alcohols of the formula (I) to product allyl alcohols of the formula (II)

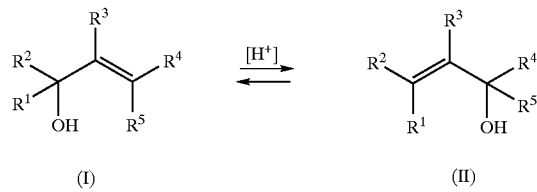

where $R^1$ to $R^5$ are hydrogen or a mono- or polyunsaturated or saturated $C_1$–$C_{12}$-alkyl radical, which may be substituted, in both directions of the equilibrium, wherein the reaction takes place in the presence of an oxoperoxotungsten(VI) complex of the formula (III),

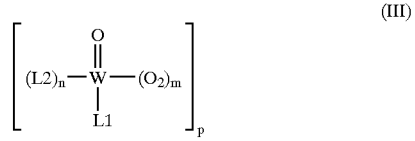

where

L1, L2 in each case independently of one another are water, hydroxyl, alkoxy or a free coordination site, or are optionally a ligand chosen from the group of aminoalcohols, aminophenols, aminocarboxylic acids or mixtures thereof or mixtures of amines with alcohols, phenols or carboxylic acids, m is the number 1 or 2 n is a number from 1 to 6 p is a number from 1 to 6, where in the case of p>1 a bi- or polynuclear complex is formed.

Examples of allyl alcohols of the formula (I) or (II) which are advantageously isomerizable using the process according to the invention are: 2-methyl-3-buten-2-ol, prenol (3-methyl-2-buten-1-ol), linalool, nerol and geraniol as well as farnesol (3,7,11-trimethyldodeca-2,6,10-trien-1-ol) and nerolidol (3,7,11-trimethyldodeca-1,6,10-trien-3-ol), in particular linalool, nerol and geraniol.

The ligands L1 and/or L2 can either be water, hydroxyl, alkoxy or a free coordination site, or optionally nitrogen- or oxygen-containing ligands such as aminoalcohols, aminophenols or aminocarboxylic acids or mixtures thereof.

Examples of aminoalcohols which may be used are: triethanolamine, diethanolamine, monoethanolamine, tripropanolamine, dipropanolamine, 3-amino-1-propanol, 1-amino-2-propanol, 2-amino-1-propanol, butyldiethanolamine, methyldiisopropanolamine, N-(2-hydroxybenzyl) amine or N,N'-bis(2-hydroxybenzyl)-1,2-diaminoethane.

Examples of aminophenols which may be used are: o-aminophenol, m-aminophenol, p-aminophenol, or 8-hydroxyquinoline optionally substituted by halogen, alkyl, amino, hydroxyl, alkoxy, thio, sulfonyl or nitro, particularly preferably 8-hydroxyquinoline.

Examples of aminocarboxylic acids which may be used are: picolinic acid, 2,6-pyridinedicarboxylic acid or β-alanine.

It is also possible to use mixtures of amines with alcohols, phenols or carboxylic acids.

Amines are understood as meaning, for example, mono-, di- or trimethylamine, ethylamine, mono-, di- or triethylamine, mono-, di- or tributylamine, preferably diethylamine.

The carboxylic acids are understood as meaning mono- or polyunsaturated or saturated mono-, di- or tricarboxylic acids having 1 to 12 carbon atoms, which may optionally be substituted by hydroxyl or halogen, for example formic acid, acetic acid, butyric acid, pivalic acid, butyric acid, [sic] hexanoic acid, lauric acid, acrylic acid, oleic acid, lactic acid, tartaric acid, citric acid, malic acid, particularly preferably citric acid.

The phenols may optionally be substituted by halogen, alkyl, amino, hydroxyl, alkoxy, thio, sulfonyl or nitro.

Preference is given to using mixtures of diethylamine and phenol or diethylamine and citric acid.

An alcohol is understood as meaning, unless stated otherwise, an alcohol ROH where R is a mono- or polyunsaturated or saturated $C_1$–$C_{15}$-alkyl radical which may be mono- or polysubstituted by halogen, $C_1$–$C_6$-alkyl, amino or hydroxyl, for example methanol, ethanol, propanol, isopropanol, butanol, tert-butanol, pentanol, geraniol, nerol, nerolidol, prenol, linalool or farnesol.

It is, however, also possible to use 1,3-aminoalcohols or 1,4-aminoalcohols as additional ligands. The aminoalcohols with a primary amine on the nitrogen atom can additionally be mono- and/or di-alkyl-substituted. The aminoalcohols with a secondary amine on the nitrogen atom can additionally be mono-alkyl-substituted.

Preferred catalysts according to the invention are those of the formulae

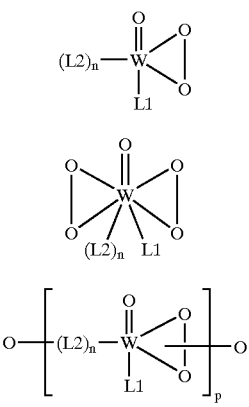

where L1 and L2 and n are as defined above, and p is a number from 2 to 6.

The invention also provides novel oxoperoxotungsten(VI) complexes of the formula (III),

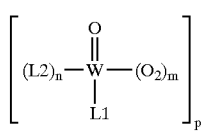

(III)

where
L1 is water, hydroxyl, alkoxy or a free coordination site, or is optionally a ligand chosen from the group of aminoalcohols, aminophenols, aminocarboxylic acids or mixtures thereof or mixtures of amines with alcohols, phenols or carboxylic acids, and
L2 is a ligand chosen from the group of aminoalcohols, aminophenols, aminocarboxylic acids or mixtures thereof or mixtures of amines with alcohols, phenols or carboxylic acids,
m is the number 1 or 2
n is a number from 1 to 6
p is a number between 1 and 6, where in the case of p>1 a bi- or polynuclear complex is formed.

Preference is given to those complexes of the formulae (IIIa), (IIIb) and (IIIc),

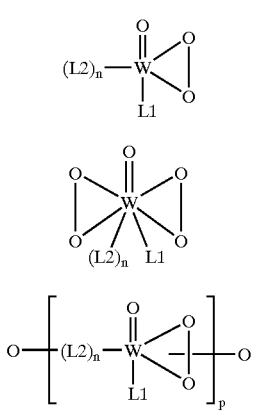

where
L1 is water, hydroxyl, alkoxy or a free coordination site, or is optionally a ligand chosen from the group of aminoalcohols, aminophenols, aminocarboxylic acids or mixtures thereof or mixtures of amines with alcohols, phenols or carboxylic acids, and
L2 is a ligand chosen from the group of aminoalcohols, aminophenols, aminocarboxylic acids or mixtures thereof or mixtures of amines with alcohols, phenols or carboxylic acids,
n is a number from 1 to 6
p is a number between 2 and 6, where in the case of p>1 a bi- or polynuclear complex is formed.

Particular preference is given to those complexes where the ligands L1 and/or L2 are 8-hydroxyquinoline.

The peroxotungsten(VI) complexes according to the invention may be in mononuclear form or in polynuclear form. If, in the case of p>1, the complexes are in bi- or polynuclear form, then the complex has the structure given in formula (IIIc).

8-Hydroxyquinoline is particularly preferably used as ligand L1 and/or L2. The molar ratio of tungsten to 8-hydroxyquinoline is in the range 1:1 to 1:5, preferably 1:1 and 1:2.

The oxoperoxotungsten(VI) complexes can be prepared according to the process described in DE 195 33 331 from tungstic acid with aqueous hydrogen peroxide solution and optional subsequent addition of the ligand(s).

The oxoperoxotungsten(VI) compounds can also be prepared under anhydrous conditions from tungstic acid and urea/hydrogen peroxide adduct and optionally subsequent addition of the ligand(s) in an alcohol ROH, where the alcohols are as defined above, preferably geraniol, nerol and linalool.

The oxoperoxotungsten(VI) complex can be prepared either separately prior to the actual reaction, or else simultaneously in situ in the precursor allyl alcohol.

In general, the oxoperoxotungsten(VI) complex is used dissolved in the precursor allyl alcohol in a concentration of from 0.001 to about 5% by weight.

The set amount of the aminoalcohol ligand and, in particular, the amount of ligand relative to the amount of oxoperoxotungsten(VI) complex used has an effect on the selectivity of the reaction.

A small amount of aminoalcohol ligand, based on the amount of tungsten, effects a lower selectivity and activity.

It has proven particularly advantageous to firstly combine the ligand L1 or L2 with or without an additional organic solvent with the aqueous or organic solution of the oxoperoxotungsten(VI) complex, and only then to add the solution or suspension of the finished catalyst prepared in this way to the precursor allyl alcohol. The additional ligand is generally used in an amount of from 1 mol % to 1000 mol %, preferably from 100 mol % to 700 mol %, based on the amount of tungsten.

The absolute concentrations of ligand and tungsten complex in the reaction mixture are unimportant in the process according to the invention and can, for example, be increased such that the rate of the establishment of an equilibrium is increased in a desired manner.

An increase in the rate of the establishment of an equilibrium can also be achieved in the process according to the invention by removing water formed as a result of secondary reactions from the mixture, for example by passing over a stream of inert gas, adding known water-removing agents, or stripping with the product allyl alcohol stream of gas during the distillation.

The process according to the invention is generally carried out at temperatures of from 50 to 300° C., preferably at 150 to 250° C.

It can be carried out with and without use of a solvent, discontinuously, or else continuously. Solvents which may be used are organic solvents, such as toluene, tetrahydrofuran, benzene, cyclohexane, xylene, methylene chloride or mesitylene, although preference is given to using the precursor allyl alcohols themselves as solvents.

The process according to the invention can advantageously be carried out if the precursor allyl alcohols in the reaction mixture are present in a concentration of from about 10% by weight to about 100% by weight.

A particularly advantageous process according to the invention is one where the precursor allyl alcohols used are geraniol and nerol, and the product allyl alcohol prepared is 2-linalool.

For work-up in this process, 2-linalool is separated off from the product mixture by distillation as the lower-boiling component. In general, precursor allyl alcohols and secondary compounds will be present in the product allyl alcohol. The product allyl alcohol can be purified by distillation in accordance with known methods.

The isomerization is an equilibrium reaction and the position of the equilibrium depends on the thermodynamic properties of the precursor allyl alcohols and product allyl alcohols, and on the reaction conditions. A discontinuous or continuous removal of linalool, the lowest-boiling allyl alcohol in the mixture, from the reaction batch permits, even in the case of an unfavorable establishment of an equilibrium as a result of the shifting of the equilibrium, a favorable space-time yield, the still of the distillation column serving as reaction chamber.

The examples below serve to describe the process according to the invention in more detail without limiting it:

Preparation of an Oxoperoxotungsten(VI) Complex

For example, tungstic acid is suspended at 40° C. in a 3.5-fold excess of aqueous hydrogen peroxide. After stirring for 6 hours, the solution is filtered. 8-Hydroxyquinoline is added to this prepared oxoperoxotungsten(VI) solution. The 8-hydroxyquinoline is added as solid or as melt, or is added dropwise dissolved in an organic solvent, e.g. alcohol. 8-Hydroxyquinoline is used in a preferred amount of from 1 to 3.5 mol equivalents, based on the tungsten. The resulting solution or suspension is used directly for the isomerization with a precursor allyl alcohol by adding it to geraniol or by adding geraniol to the catalyst mixture. The complex compound of tungsten oxoperoxo and 8-hydroxyquinoline can, however, also be isolated as solid. Mixtures of aqueous oxoperoxotungsten(VI) solution and alcoholic 8-hydroxyquinoline solution are concentrated by evaporation. The precipitated catalyst powder is filtered off and dried after washing. It is also possible to extract, by known methods, the catalyst mixture of oxoperoxotungsten(VI) and 8-hydroxyquinoline prepared by the method described above, and to strip off the extractant. The catalyst complex can likewise by precipitated by the addition of the solvent in which the complex compound is itself sparingly soluble, e.g. geraniol. However, it is also possible, in any order, to add 8-hydroxyquinoline and oxoperoxotungsten(VI) solution separately one after the other, or simultaneously to the precursor allyl alcohol. The novel tungsten complex prepared by processes described above contains a peroxo group and 8-hydroxyquinoline as further ligands and is notable for the fact that the ratio of tungsten to 8-hydroxyquinoline is 1:1 or 1:2.

This catalyst can be added to the precursor allyl alcohol at temperatures of from 20 to 300° C. dissolved in any desired solvent or as a solid.

The water present in the catalyst solution or suspension and the organic solvent are advantageously removed by distillation together with the isomerization product, e.g. with the lower-boiling linalool.

Isomerization

The experiments for the isomerization of geraniol and nerol to give 2-linalool were carried out in a 100 ml three-necked glass flask as reaction chamber fitted with internal thermometer, distillation bridge, gas feed pipe and a magnetic stirrer. The reaction flask was heated for the reaction in a silicone oil bath, and a continuous stream of 1 l/h of argon or nitrogen was passed over the stirred reaction solution. Precursor allyl alcohol was added to the calculated catalyst solution, and the mixture was heated with stirring until the required temperature was reached. The experiments were ended after 1 hour by cooling, and the product composition was determined by means of GC. No product was distilled off during the reactions.

The catalyst solution was prepared by suspending 24 g (212 mmol) of tungstic acid in 30% strength by weight hydrogen peroxide solution. The yellow suspension was stirred for 6 h at 40° C. and, after cooling, the cloudy solution was filtered. This oxoperoxotungsten(VI) complex solution was ready to use for the isomerization, and the calculated amount of a ligand could be added thereto. In the case of 8-hydroxyquinoline as ligand, the ligand was added as ethanolic solution. Alternatively, the oxoperoxotungsten (VI) solution can also be added to the solution of the ligand.

Effect of Bases as Ligands

EXAMPLES 1 TO 10

A 100 ml three-necked glass flask was charged with 120 mg (0.12 mmol of W content) of the aqueous oxoperoxotungsten(VI) solution and, successively, 0.24 mmol of the additional ligand shown in Table 1 below, and 20 g (0.13 mol) of geraniol at room temperature. The mixture was heated to 200° C. in an oil bath with stirring and, throughout the reaction time of 1 hour, a 2 l/h stream of argon was passed over the solution. The reaction was stopped after 1 hour by cooling.

Subsequent gas-chromatographic analysis (GC) of the reaction mixture produced the result given in Table 1.

TABLE 1

| Ex. | Ligand | Geraniol [GC area %] | Nerol [GC area %] | 2-Linalool [GC area %] | Low-boiling components [GC area %] | Medium-boiling components [GC area %] | High-boiling components [GC area %] | 2-Linalool selectivity [%] |
|---|---|---|---|---|---|---|---|---|
| 1 | None | 94.2 | 2.60 | 1.03 | 0.81 | 0.07 | 1.28 | 32 |
| 2 | Diethylamine | 37.85 | 1.65 | 13.43 | 12.14 | 2.34 | 32.59 | 22 |
| 3 | Pyridine | 11.78 | 1.41 | 14.14 | 22.04 | 3.51 | 47.12 | 16 |
| 4 | Imidazole | 78.15 | 2.63 | 15.07 | 0.82 | 0.21 | 3.12 | 78 |

TABLE 1-continued

| Ex. | Ligand | Geraniol [GC area %] | Nerol [GC area %] | 2-Linalool [GC area %] | Low-boiling components [GC area %] | Medium-boiling components [GC area %] | High-boiling components [GC area %] | 2-Linalool selectivity [%] |
|---|---|---|---|---|---|---|---|---|
| 5 | Poly-(4-vinyl-pyridine) | 80.64 | 2.51 | 11.03 | 1.83 | 0.46 | 3.53 | 65 |
| 6 | 1-Amino-2-propanol | 51.44 | 4.35 | 32.58 | 3.03 | 0.81 | 7.79 | 74 |
| 7 | 8-Hydroxy-quinoline | 38.66 | 8.67 | 44.60 | 1.49 | 0.43 | 6.15 | 85 |
| 8 | Quinoline | 3.80 | 0.69 | 7.78 | 21.32 | 4.83 | 61.58 | 8 |
| 9 | Bispyridyl | 3.10 | 0.51 | 5.31 | 23.52 | 4.96 | 62.60 | 6 |
| 10 | o-Aminophenol | 0.22 | 0.00 | 0.97 | 28.30 | 5.96 | 64.55 | 1 |

Without the addition of ligands, the oxoperoxotungsten (VI) catalyst displays low isomerization activity. With 8-hydroxyquinoline the isomerization of geraniol to linalool proceeds not only at the fastest rate, but also in the most selective manner. In the presence of amines alone, conversions and selectivities are poorer than without the addition of amine.

Effect of the Concentration of the Ligand Using 8-hydroxyquinoline as an Example

EXAMPLES 11 TO 17

A 100 ml three-necked glass flask was charged with 120 mg (0.12 mmol) of the aqueous oxoperoxotungsten(VI) solution, and 8-hydroxyquinoline was added in the molar ratio shown in Table 2 below, and 20 g (0.13 mol) of geraniol were added at room temperature. The mixture was heated at 200° C. for 1 hour while passing over a continuous stream of argon. Subsequent GC of the reaction mixture produced the result shown in Table 2.

The optimum tungsten: 8-hydroxyquinoline molar ratio with regard to selectivity and activity is in a range from 1:2 to 1:5.

Effect of Temperature

EXAMPLES 18 TO 20

A 100 ml three-necked glass flask was charged with 120 mg (0.12 mmol) of the aqueous oxoperoxotungsten(VI) solution and, successively, 66 mg (0.455 mmol) of 8-hydroxyquinoline and 20 g (0.13 mol) of geraniol were added at room temperature. The mixture was heated to the temperature shown in Table 3 in an oil bath in a stream of argon with stirring. Subsequent GC of the reaction mixture produced the result shown in Table 3.

TABLE 2

| Ex. | W:8-hydroxyquinoline molar ratio | Geraniol [GC area %] | Nerol [GC area %] | 2-Linalool [GC area %] | Low-boiling components [GC area %] | Medium-boiling components [GC area %] | High-boiling components [GC area %] | 2-Linalool selectivity [%] |
|---|---|---|---|---|---|---|---|---|
| 11 | 1:1 | 36.18 | 7.94 | 40.24 | 2.56 | 0.77 | 12.31 | 72 |
| 12 | 1:2 | 38.66 | 8.67 | 44.60 | 1.49 | 0.43 | 6.15 | 85 |
| 13 | 1:3 | 31.66 | 10.36 | 49.17 | 1.34 | 0.49 | 6.98 | 85 |
| 14 | 1:3.5 | 36.25 | 9.04 | 48.68 | 0.99 | 0.41 | 4.63 | 89 |
| 15 | 1:4 | 40.65 | 7.98 | 44.73 | 1.09 | 0.38 | 5.17 | 87 |
| 16 | 1:5 | 32.63 | 10.15 | 50.20 | 1.00 | 0.45 | 5.57 | 88 |
| 17 | 1:7 | 30.08 | 15.12 | 44.09 | 1.35 | 0.41 | 8.95 | 80 |

TABLE 3

| Ex. | Temperature (° C.) | Geraniol [GC area %] | 2-Linalool [GC area %] | Nerol [GC area %] | Low-boiling component [GC area %] | Medium-boiling component [GC area %] | High-boiling component [GC area %] | 2-Linalool selectivity [%] |
|---|---|---|---|---|---|---|---|---|
| 18 | 170 | 59.65 | 32.16 | 4.05 | 0.78 | 0.2 | 3.16 | 89 |
| 19 | 180 | 56.89 | 34.79 | 4.73 | 0.57 | 0.19 | 2.85 | 91 |
| 20 | 190 | 34.10 | 49.21 | 8.69 | 1.28 | 0.42 | 6.03 | 86 |

At temperatures below 200° C., with 8-hydroxyquinoline, the rates of reaction decrease with temperature. The highest selectivity for the isomerization was found at a temperature of 180° C. In this case, the isomerization still proceeded at a good rate.

Effect of Catalyst Preparation

EXAMPLE 21 AND EXAMPLE 7 (Comparative Example)

The catalyst oxoperoxotungsten(VI) was prepared in an anhydrous alcoholic solution by stirring tungstic acid in a 3.3-fold molar excess of an ethanolic solution of urea/hydrogen peroxide adduct at 40° C. for 20 hours. The determination of the tungsten content of the filtered homogeneous solution produced 90% of the theoretical value of tungsten. Analogously to Example 7, 0.12 mmol of the catalyst solution was initially introduced and, successively, a 3.5-fold molar excess of 8-hydroxyquinoline and 20 [lacuna] of geraniol were added. The reaction flask was heated at 200° C. for 1 hour in a stream of argon.

TABLE 4

| Ex. | Catalyst solvent | Geraniol [GC area %] | Nerol [GC area %] | 2-Linalool [GC area %] | Low-boiling component [GC area %] | Medium-boiling component [GC area %] | High-boiling component [GC area %] | 2-Linalool selectivity [%] |
|---|---|---|---|---|---|---|---|---|
| 7 | $H_2O_2$ in water | 38.66 | 8.67 | 44.60 | 1.49 | 0.43 | 6.15 | 85 |
| 21 | Urea $xH_2O_2$ in EtOH | 40.76 | 7.66 | 45.29 | 0.78 | 0.36 | 5.16 | 88 |

The oxoperoxotungsten(VI) catalyst prepared under anhydrous conditions in ethanol from tungstic acid and urea/hydrogen peroxide adduct displays, under the conditions of the isomerization, activity and selectivity which are as good as those for the catalyst prepared in aqueous hydrogen peroxide.

Effect of Precursor Allyl Alcohol

EXAMPLE 22 AND EXAMPLE 14

Analogously to Example 14, the reaction was carried out with isomerically pure nerol. Reaction conditions and precursor and catalyst compositions were identical to Example 14.

TABLE 5

| Ex. | W:8-hydroxy-quinoline molar ratio | Geraniol [GC area %] | Nerol [GC area %] | 2-Linalool [GC area %] | Low-boiling component [GC area %] | Medium-boiling component [GC area %] | High-boiling component [GC area %] | 2-Linalool selectivity [%] |
|---|---|---|---|---|---|---|---|---|
| 14 | 1:3.5 | 36.25 | 9.04 | 48.68 | 0.99 | 0.41 | 4.63 | 89 |
| 22 | 1:3.5 | 11.82 | 32.97 | 44.14 | 3.37 | 0.85 | 6.85 | 80 |

The isomerization of nerol to linalool proceeds as well as that with geraniol. During the isomerization, by establishing the equilibrium with respect to linalool, geraniol is also formed from nerol, and correspondingly nerol is also formed from geraniol.

Synthesis of the oxoperoxotungsten catalysts and the use thereof in the isomerization of geraniol and nerol:

Synthesis:

EXAMPLE 23

To a solution of 9.896 g of 8-hydroxyquinoline in 160 ml of ethanol are added, at room temperature and with stirring, 19.5 g of an aqueous oxoperoxotungsten(VI) solution (tungsten content: 19% by weight). The clear solution immediately turns intense yellow and, after the further addition of 90 ml of ethanol, approximately 10 g of a yellow crystalline powder precipitate out over the course of a few hours. The crystals are washed with a small amount of ethanol and dried in the air.

Microanalysis: C: 39.1%; O: 19.3%; N: 5.0%; H: 2.7%; W: 30.6%

EXAMPLE 24

10 ml of ethanol and 190 mg (1.31 mmol) of 8-hydroxyquinoline in 3 ml of ethanol are added successively to 1.2 g of an aqueous oxoperoxotungsten(VI) solution (comprising 1.2 mmol of tungsten). The initially colorless solution momentarily turns intense yellow and remains clear. 70 ml of geraniol or 70 ml of nerol or a mixture of geraniol and nerol is added to this yellow solution at room temperature and stirred. Within minutes, the solution changes from yellow via orange to red-brown, and 126 mg of a red-brown, fine crystalline precipitate form.

Microanalysis: C: 30.7%; O: 16%; N: 3.9%; H: 2.2%; W: 46%

Catalysis:

EXAMPLE 25

250 g of a geraniol/nerol mixture in the ratio 2:1 were introduced into a 500 ml stirred flask fitted with baffles, paddle stirrer and distillation bridge, and heated to 180° C. in a stream of argon (1.3 l/h). At elevated temperature, 900 mg of the catalyst powder from Example 23 were added and the mixture was stirred for one hour at 180° C. Subsequent GC of the reaction mixture gave the result shown in Table 6.

EXAMPLE 26

A 100 ml three-necked glass flask was charged with 17.7 mg of the catalyst powder from Example 24, and 7 g of isomerically pure geraniol were added. The mixture was heated to 180° C. in an oil bath in a stream of argon with stirring. After one hour, subsequent GC analysis of the reaction mixture produced the result shown in Table 6.

TABLE 6

| Ex. | Catalyst from example | Geraniol [GC area %] | Nerol [GC area %] | 2-Linalool [GC area %] | Low-boiling component [GC area %] | Medium-boiling component [GC area %] | High-boiling component [GC area %] | 2-Linalool selectivity [%] |
|---|---|---|---|---|---|---|---|---|
| 25 | 23 | 36.16 | 17.03 | 42.18 | 1.48 | 0.25 | 3.03 | 90 |
| 26 | 24 | 47.74 | 5.42 | 42.54 | 0.94 | 0.15 | 3.22 | 91 |

Depending on the excess of 8-hydroxyquinoline, based on tungsten, different oxoperoxotungsten complexes formed which were characterized by elemental analysis and IR spectroscopy. Both catalyst species are catalytically active with comparable selectivities with regard to the formation of linalool from geraniol and nerol.

General Explanation of the Results:

After the reaction had been ended by cooling, the product composition was determined by means of GC. The low-boiling components were dehydration products from geraniol, nerol and linalool. High-boiling components were formed as a result of ether formation from geraniol, nerol and linalool. The linalool selectivity was determined from the quotient of the conversion to linalool and the sum of the products linalool, low-boiling components, medium-boiling components and high-boiling components.

We claim:

1. A process for the isomerization of precursor allyl alcohols of the formula (I) to product allyl alcohols of the formula (II)

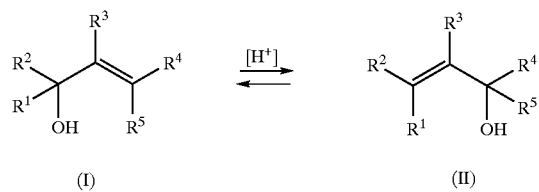

where $R^1$ to $R^5$ are hydrogen or a mono- or polyunsaturated or saturated $C_1$–$C_{12}$-alkyl radical, which may be substituted, in both directions of the equilibrium, wherein the reaction takes place in the presence of an oxoperoxotungsten(VI) complex of the formula (III),

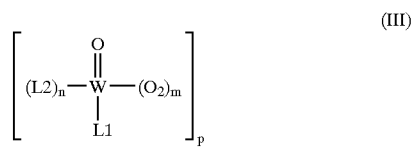

where

L1, L2 in each case independently of one another are water, hydroxyl, alkoxy or a free coordination site, or are optionally a ligand chosen from the group of aminoalcohols, aminophenols, aminocarboxylic acids or mixtures thereof or mixtures of amines with alcohols, phenols or carboxylic acids, m is the number 1 or 2 n is a number from 1 to 6 p is a number from 1 to 6, where in the case of p>1 a bi- or polynuclear complex is formed.

2. A process as claimed in claim 1, wherein the complex of the formula (III) is chosen from the group of the formulae (IIIa), (IIIb) and (IIIc)

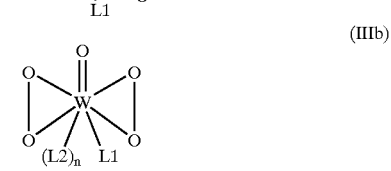

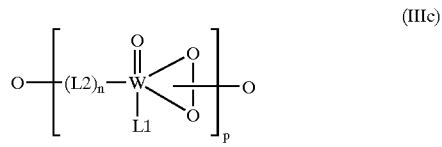

where L1, L2 and n are as defined in claim 1, and p is a number from 2 to 6.

3. A process as claimed in claim 1, wherein L1 and/or L2 are chosen from the group triethanolamine, diethanolamine, monoethanolamine, tripropanolamine, dipropanofamine, 3-amino-1-propanol, 1-amino-2-propanol, 2-amino-1-propanol, butyldiethanolamine, methyldiisopropanolamine, N-(2-hydroxybenzyl)amine and N,N'-bis(2-hydroxybenzyl)-1,2-diaminoethane.

4. A process as claimed in claim 1, wherein L1 and/or L2 are chosen from the group o-aminophenol, m-aminophenol, p-aminophenol, 8-hydroxyquinoline optionally substituted by halogen, alkyl, amino, hydroxyl, alkoxy, thio, sulfonyl or nitro, picolinic acid, 2,6-pyridinedicarboxylic acid and β-alanine.

5. A process as claimed in claim 1, wherein L1 and/or L2 are mixtures of diethylamine and phenol or diethylamine and citric acid.

6. A process as claimed in claim 1, wherein L1 and/or L2 are 8-hydroxyquinoline.

7. A process as claimed in claim 1, wherein the ratio of tungsten to 8-hydroxyquinoline is between 1:1 and 1:5.

8. A process as claimed in claim 1, wherein primary or secondary allyl alcohols are used as precursor allyl alcohol.

9. A process as claimed in claim 1, wherein the allyl alcohols are chosen from the group 2-methyl-3-buten-2-ol, prenol (3-methyl-2-buten-1-ol), linalool, nerol, geraniol, farnesol (3,7,11-trimethyldodeca-2,6,10-trien-1-ol) and nerolidol (3,7,11-trimethyldodeca-1,6,10-trien-3-ol).

10. A process as claimed in claim 1, wherein the precursor allyl alcohols are chosen from the group geraniol and nerol.

11. A process as claimed in claim 1, wherein the oxoperoxotungsten(VI) complex of the formula (III) is prepared prior to the reaction or in situ in the precursor allyl alcohol.

12. An oxoperoxotungsten(VI) complex of the formula (III),

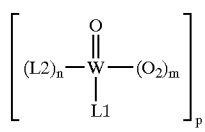
(III)

where

L1 is water, hydroxyl, alkoxy or a free coordination site, or is optionally a ligand chosen from the group of aminoalcohols, aminophenols, aminocarboxylic acids or mixtures thereof or mixtures of amines with alcohols, phenols or carboxylic acids, and L2 is a ligand chosen from the group of aminoalcohols, aminophenols, aminocarboxylic acids or mixtures thereof or mixtures of amines with alcohols, phenols or carboxylic acids, m is the number 1 or 2 n is a number from 1 to 6 p is a number between 1 and 6.

13. An oxoperoxotungsten(VI) complex as claimed in claim 12, which is chosen from the formulae (IIIa), (IIIb) and (IIIc),

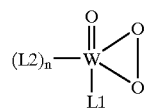
(IIIa)

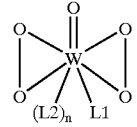
(IIIb)

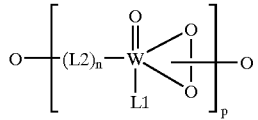
(IIIc)

where

L1 is water, hydroxyl, alkoxy or a free coordination site, or is optionally a ligand chosen from the group of aminoalcohols, aminophenols, aminocarboxylic acids or mixtures thereof or mixtures of amines with alcohols, phenols or carboxylic acids, and L2 is a ligand chosen from the group of aminoalcohols, aminophenols, aminocarboxylic acids or mixtures thereof or mixtures of amines with alcohols, phenols or carboxylic acids, n is a number from 1 to 6 p is a number between 2 and 6.

14. An oxoperoxotungsten(VI) complex as claimed in claim 12, wherein L1 and/or L2 are 5-hydroxyquinoline.

* * * * *

UNITED STATES PATENT AND TRADEMARK OFFICE
CERTIFICATE OF CORRECTION

PATENT NO.       : 6,989,468 B2                                          Page 1 of 1
APPLICATION NO.  : 10/380116
DATED            : January 24, 2006
INVENTOR(S)      : Haese et al.

It is certified that error appears in the above-identified patent and that said Letters Patent is hereby corrected as shown below:

Col. 16     lines 33-34

Claim 14 should correctly recite "...8-hydroxyquinoline," as follows:

14. An oxoperoxotungsten (VI) complex as claimed in claim 12 wherein L1 and/or L2 are 8-hydroxyquinoline.

Signed and Sealed this

Twenty-second Day of August, 2006

JON W. DUDAS
*Director of the United States Patent and Trademark Office*